United States Patent [19]

Vorbruggen et al.

[11] Patent Number: 5,374,654
[45] Date of Patent: Dec. 20, 1994

[54] 9-SUBSTITUTED CARBACYCLIN DERIVATIVES, PROCESSES FOR THEIR PREPARATION, AND THEIR USE AS MEDICINAL AGENTS

[75] Inventors: Helmut Vorbruggen; Ulrich Klar; Bob Nieuweboer; Claus-Steffen Sturzebecher, all of Berlin, Germany

[73] Assignee: Schering Aktiengesellschaft, Berlin and Bergkamen, Germany

[21] Appl. No.: 49,649

[22] Filed: Apr. 21, 1993

Related U.S. Application Data

[63] Continuation of Ser. No. 688,137, Apr. 19, 1991, abandoned, which is a continuation-in-part of Ser. No. 332,845, Mar. 22, 1989, Pat. No. 5,053,400.

[30] Foreign Application Priority Data

Jul. 24, 1987 [DE] Germany .................. 3725031

[51] Int. Cl.$^5$ .................. C07C 405/00; A61K 31/557
[52] U.S. Cl. ..................... 514/530; 514/374; 514/452; 514/561; 514/567; 514/564; 514/573; 514/657; 514/659; 514/681; 514/691; 548/237; 548/238; 549/373; 549/374; 549/415; 560/39; 560/56; 560/116; 560/119; 562/444; 562/466; 562/498; 562/501
[58] Field of Search .................. 562/501; 514/572, 530, 514/573; 560/119

[56] References Cited

U.S. PATENT DOCUMENTS

| | | | |
|---|---|---|---|
| 4,487,960 | 12/1984 | Lin | 562/501 X |
| 4,588,823 | 5/1986 | Aristoff | 562/501 X |
| 4,971,987 | 11/1990 | Vorbrueggen et al. | 549/373 X |
| 5,053,400 | 10/1991 | Vorbruggen et al. | 514/150 |
| 5,162,353 | 11/1992 | Vorbruggen et al. | 560/119 |

FOREIGN PATENT DOCUMENTS

| | | |
|---|---|---|
| 0086611 | 8/1983 | European Pat. Off. . |
| 0224275 | 6/1987 | European Pat. Off. . |
| 3428266 | 1/1986 | Germany . |

OTHER PUBLICATIONS

The Merck Index, 11th Ed., (1989), p. 2728.

*Primary Examiner*—Joseph Paul Brust
*Attorney, Agent, or Firm*—Millen, White, Zelano, & Branigan

[57] ABSTRACT

The invention relates to carbacyclin derivatives of Formula I

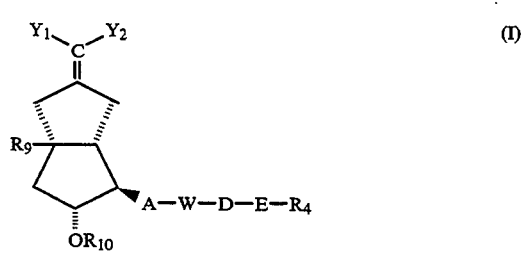

wherein the various substituents are defined herein, including, inter alia,
if $R_2$ is a hydrogen atom, their salts with physiologically compatible bases, their cyclodextrin clathrates, and their use as medicinal agents.

10 Claims, No Drawings

9-SUBSTITUTED CARBACYCLIN DERIVATIVES, PROCESSES FOR THEIR PREPARATION, AND THEIR USE AS MEDICINAL AGENTS

This application is a continuation of application Ser. No. 07/688,137, filed Apr. 19, 1991, now abandoned which is a continuation-in-part of Ser. No. 07/332,845, filed Mar. 22, 1989, now U.S. Pat. No. 5,053,400.

The invention relates to novel 9-substituted carbacyclin derivatives, processes for their preparation, as well as their use as medicinal agents.

U.S. Pat. No. 4,420,632 describes 9-alkylated carbacyclin derivatives exhibiting antithrombotic, antisecretory and bronchodilating properties. They show furthermore thrombocyte-aggregation-inhibiting activity.

It has been found that carbacyclin analogs chain-lengthened in the 9-position and having a reactive group in the ω-position can be bound to polymeric carriers with an only small loss of biological activity. The compounds according to this invention are suitable for inhibiting thrombocyte aggregation, for lowering blood pressure via vasodilation, for inhibiting gastric acid secretion, as well as, after chemical linkage to proteins, for the preparation of antibodies to carbacyclins.

The invention concerns carbacyclin derivatives of Formula I

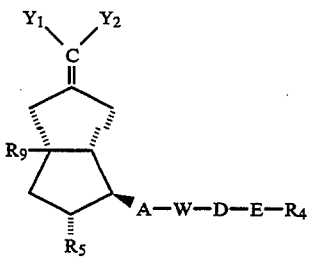

wherein
$Y_1$ is the residue —$CH_2$—X—$(CH_2)_n$—$R_1$ or the residue

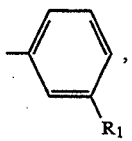

n is 1 or 3,
$R_1$ is the residue

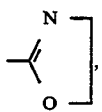

the residue

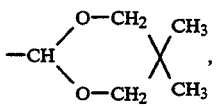

—$COCH_3$, $COOR_2$ wherein $R_2$ can mean hydrogen or alkyl of 1-10 carbon atoms optionally substituted by halogen, phenyl, $C_1$-$C_4$-alkoxy or $C_1$-$C_4$-dialkylamino, cycloalkyl, aryl, or a heterocyclic residue; or the residue $CONHR_3$ wherein $R_3$ means hydrogen or an alkanoyl or alkanesulfonyl residue of respectively 1-10 carbon atoms, $R_9$ is the residue —Z—$(CH_2)_m$—$R_6$,
m is 2-10,
Z is a —C≡C—, a cis-CH=CH—, a trans-CH=CH— or a —$CH_2$—$CH_2$-group,
$R_6$ is $N_3$, Cl, Br, I as well as $COOR_2$ if Z means —C≡C—, cis-CH=CH— or trans-CH=CH—,
$R_2$ is hydrogen or a methyl or ethyl group,
X is an oxygen atom or a methylene group,
$Y_2$ is hydrogen or fluorine,
A is a —$CH_2$—$CH_2$—, trans-CH=CH— or —C≡C-group,
W is a free or functionally modified hydroxymethylene group or a free or functionally modified

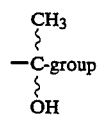

wherein the OH-group can be in the α- or β-position,
D is the group

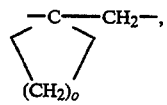

a straight-chain, saturated alkylene group of 1-5 carbon atoms, a branched, saturated or a straight-chain or branched, unsaturated alkylene group of 2-5 carbon atoms which can optionally be substituted by fluorine atoms,
o is 1, 2 or 3,
E is a direct bond, a —C≡C-group or a —CH=$CR_7$-group wherein $R_7$ means a hydrogen atom, an alkyl group of 1-5 carbon atoms or halogen,
$R_4$ is an alkyl group of 1-10 carbon atoms, a cycloalkyl group of 3-10 carbon atoms, or an optionally substituted aryl group of 6-10 carbon atoms, or a heterocyclic group,
$R_5$ is a free or functionally modified hydroxy group, and, if $R_2$ means a hydrogen atom,
their salts with physiologically compatible bases, and their cyclodextrin clathrates.

Suitable alkyl groups $R_2$ are considered to be straight- or branched-chain alkyl groups of 1-10 carbon atoms, such as, for example, methyl, ethyl, propyl, isopropyl, butyl, isobutyl, tert-butyl, pentyl, isopentyl, neopentyl, heptyl, hexyl, decyl.

The alkyl groups $R_2$ can optionally be mono- to polysubstituted by halogen atoms, $C_1$-$C_4$-alkoxy groups, phenyl and di-$C_1$-$C_4$-alkylamines. Those alkyl groups that are monosubstituted are preferred.

Examples of substituents are fluorine, chlorine or bromine atoms, phenyl, dimethylamino, diethylamino, methoxy, ethoxy. Preferred alkyl groups $R_2$ are those of 1-4 carbon atoms, such as, for example, methyl, ethyl, propyl, dimethylaminopropyl, isobutyl, butyl.

Suitable aryl groups $R_2$ are substituted as well as unsubstituted aryl groups, e.g. phenyl, 1-naphthyl and 2-naphthyl, each of which can be substituted by 1-3 halogen atoms, a phenyl group, 1-3 alkyl groups of 1-4 carbon atoms each, a chloromethyl, fluoromethyl, trifluoromethyl, carboxy, hydroxy or alkoxy group of 1-4 carbon atoms.

The substituents in the 3- and 4-positions on the phenyl ring are preferred, e.g. by fluorine, chlorine, alkoxy or trifluoromethyl or in the 4-position by hydroxy.

The cycloalkyl group $R_2$ can contain in the ring 4-10, preferably 5 and 6 carbon atoms. The rings can be substituted by alkyl groups of 1-4 carbon atoms. Examples that can be cited are cyclopentyl, cyclohexyl, methylcyclohexyl and adamantyl.

Suitable heterocyclic groups $R_2$ are 5- and 6-membered heterocycles containing at least one hetero atom, preferably nitrogen, oxygen or sulfur. Examples that can be cited are 2-furyl, 3-furyl, 2-thienyl, 3-thienyl, 2-pyridyl, 3-pyridyl, 4-pyridyl, and others.

The acid residue $R_3$ can be physiologically compatible acid residues. Preferred acids are organic carboxylic acids and sulfonic acids of 1-10 carbon atoms pertaining to the aliphatic, cycloaliphatic, aromatic, aromatic-aliphatic and heterocyclic series. These acids can be saturated, unsaturated and/or polybasic and/or substituted in the usual way. Examples of substituents are $C_1$-$C_4$-alkyl, hydroxy, $C_1$-$C_4$-alkoxy, oxo or amino groups, or halogen atoms (F, Cl, Br).

The following carboxylic acids can be cited as examples: formic acid, acetic acid, propionic acid, burytic acid, isobutyric acid, valeric acid, isovaleric acid, caproic acid, enanthic acid, capryiic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy or carboxy groups, nicotinic acid, isonicotinic acid, furan-2-carboxylic acid, cyclopentylpropionic acid. Especially preferred acyl residues are considered to be those of up to 4 carbon atoms. Examples of sulfonic acids are methanesulfonic acid, ethanesulfonic acid, isopropanesulfonic acid, cyclohexanesulfonic acid, N,N-dimethylaminosulfonic acid, N,N-diethylaminosulfonic acid, N,N-bis($\beta$-chloroethyl)aminosulfonic acid, N,N-diisobutylaminosulfonic acid, N,N-dibutylaminosulfonic acid, pyrrolidino-, piperidino-, piperazino-, N-methylpiperazino- and morpholinosulfonic acids, sulfonic acids of up to 4 carbon atoms being especially preferred.

The hydroxy groups $R_5$ and those in W can be functionally modified, e.g. by etherification or esterification, wherein the free or modified hydroxy groups in W can be in the $\alpha$- or $\beta$-position, free hydroxy groups being preferred.

Suitable ether and acyl residues are those known to persons skilled in the art. Preferred are readily cleavable ether residues, such as, for example, the tetrahydropyranyl, tetrahydrofuranyl, $\alpha$-ethoxyethyl, trimethylsilyl, dimethyl-tert-butylsilyl, and tri-p-benzylsilyl residues. Suitable acyl residues are the same as mentioned for $R_3$; examples that can be cited by name are acetyl, propionyl, butyryl, benzoyl.

The alkyl group $R_4$ can represent straight- and branched-chain, saturated and unsaturated alkyl residues, preferably saturated ones, of 1-10, especially 1-4 carbon atoms.

Examples are methyl, ethyl, propyl, butyl, isobutyl, tert-butyl, pentyl, hexyl, heptyl, octyl, butenyl, isobutenyl, propenyl, pentenyl, hexenyl.

The cycloalkyl group $R_4$ can contain in the ring 3-10, preferably 5 and 6 carbon atoms. The rings can be substituted by alkyl groups of 1-4 carbon atoms. Examples are cyclopentyl, cyclohexyl, methylcyclohexyl and adamantyl.

Examples of substituted and, respectively, unsubstituted aryl groups $R_4$ are: phenyl, 1-naphthyl and 2-naphthyl, each of which can be substituted by 1-3 halogen atoms, a phenyl group, 1-3 alkyl groups of 1-4 carbon atoms each, a chloromethyl, fluoromethyl, trifluoromethyl, carboxy, $C_1$-$C_4$-alkoxy or hydroxy group. The substitution in the 3- and 4-positions on the phenyl ring is preferred, for example, by fluorine, chlorine, $C_1$-$C_4$-alkoxy or trifluoromethyl, or in the 4-position by hydroxy.

Suitable heterocyclic groups $R_4$ can be 5- and 6-membered heterocycles containing at least one hetero atom, preferably nitrogen, oxygen or sulfur. Examples that can be cited are 2-furyl, 2-thienyl, 2-pyridyl, 3-pyridyl, 4-pyridyl, 3-furyl, 3-thienyl, etc.

Suitable as the alkylene group D are straight-chain or branched-chain, saturated and unsaturated alkylene residues, preferably saturated ones of up to 5 carbon atoms which can optionally be substituted by fluorine atoms, 1,2-methylene, 1,1-trimethylene, 1,1-tetramethylene or 1,1-pentamethylene. Examples are: methylene, fluoromethylene, ethylene, 1,2-propylene, ethylethylene, trimethylene, tetramethylene, pentamethylene, 1-methyltetramethylene, 1-methyltrimethylene, 1,1-trimethylenethylene, 1,1-tetramethylenethylene.

Especially preferred compounds of this invention are those wherein E stands for —C≡C— or —CH=CR$_7$ wherein $R_7$ is an alkyl group of 1-5 carbon atoms.

Suitable for the alkyl group $R_7$ of 1-5 carbon atoms are the groups already recited for the alkyl group $R_4$.

$R_7$ in the meaning of halogen is fluorine, chlorine and bromine.

Suitable for $R_9$ as —Z—(CH$_2$)$_m$—R$_6$ are alkyne or alkylene groups of 2-20 carbon atoms, wherein m=2-20, e.g. —C≡C(CH$_2$)$_m$—N , —C≡C—(CH$_2$)$_m$—CO$_2$H, —C≡C—(CH$_2$)$_m$—Br.

Suitable for salt formation with the free acids ($R_2$=H) are inorganic and organic bases as they are familiar to one skilled in the art for the formation of physiologically compatible salts. Examples that can be cited are: alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hdyroxymethyl)methylamine, etc.

The invention furthermore concerns processes for the preparation of the carbacyclins according to general Formula I of this invention, characterized in that (a) a compound of Formula IV

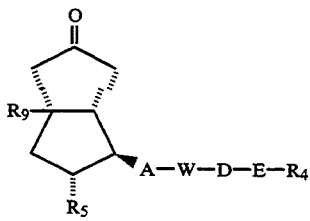

(IV)

wherein A, W, D, E, R$_4$, R$_5$ and R$_9$ have the meanings given above, and is reacted, in the presence of potassium tert-butylate, with a Wittig reagent of general Formulae V and VI or with a dianion of Formula VII

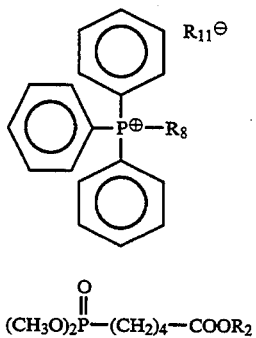

(V)

$(CH_3O)_2\overset{O}{\overset{\|}{P}}-(CH_2)_4-COOR_2$ (VI)

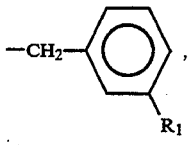

(VII)

wherein
R$_2$ has the meanings given above and
R$_8$ means the residues —CH$_2$—CH$_2$—X—(CH$_2$)$_n$—R$_1$ or

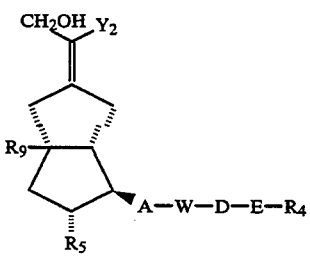

with the above-mentioned meanings for X, n and R$_1$, and
R$_{11}$ means bromine or chlorine; or (b) a compound of Formula VIII, obtained from the corresponding 4-ester by DIBAL-H reduction,

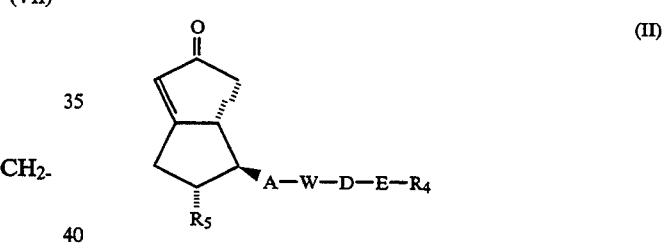

(VIII)

wherein A, W, D, E, R$_4$, R$_5$, R$_9$ and Y$_2$ have the meanings given above, is etherified in the presence of a base, optionally after blocking any free hydroxy or amino groups present, with a haloalkanoic acid derivative of Formula IX

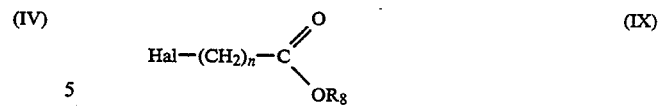

(IX)

wherein
n is 1 or 3,
Hal is a chlorine or bromine atom, and
R$_8$ is an alkyl residue of 1–4 carbon atoms or an alkali metal, and optionally subsequently, in any desired sequence, isomers are separated and/or blocked hydroxy groups are liberated and/or free hydroxy groups are esterified, etherified and/or a free carboxy group is esterified and/or an esterified carboxy group is saponified or a carboxy group is converted into an amide or, with a physiologically compatible base, into a salt.

The reaction of the compound of general Formula VIII with a haloalkanoic acid derivative of general Formula IX is carried out at temperatures of 0° C. to 100° C., preferably 10° C. to 80° C., in an aprotic solvent or solvent mixture, for example dimethyl sulfoxide, dimethylformamide, tetrahydrofuran, etc. Suitable bases are those known to one skilled in the art for etherifications, e.g. sodium hydride, potassium tert-butylate, butyllithium, etc.

The starting compounds of Formula IV are obtained by reacting compounds of Formula II

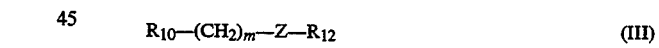

(II)

wherein R$_4$, R$_5$, A, W, D, E, Z$_1$, Z$_2$, m, o, p, q have the above-indicated meanings, with metal reagents of Formula III $R_{10}—(CH_2)_m—Z—R_{12}$ (III)

wherein R$_{12}$ means MgBr, MgCl, MgI or Al(Alkyl)$_2$ with Alkyl meaning a straight- or branched-chain alkyl residue of up to 6 carbon atoms, by 1,4-addition and subsequent introduction of the upper side chain by Wittig reaction of the 5-ring carbonyl group and conversion of group R$_{10}$ into group R$_6$. Suitable for the group R$_{10}$ are blocked amino groups, such as amino groups, for example, which are blocked by 1,1,4,4-tetramethyl-1,4-dichlorodisilylethane or by phthalic acid anhydride or, respectively, by other typical amino blocking groups, as well as hydroxy groups blocked by tert-butyldiphenylsilyl or THP groups, as well as carboxy groups blocked by conversion into otho esters or oxazoline.

After splitting off the blocking groups from the nitrogen and/or after chemical conversion of the hydroxy or amide groups into amino groups, the desired substituents R$_6$=NH$_2$ are obtained. The Mitsunobu reaction (see Synthesis 1, 1981) and, respectively, the reduction of the azide to the amine can be utilized for this conversion of a hydroxy group into an amino group.

Saponification of the carbacyclin esters is performed according to the methods known to persons skilled in the art, for example with alkaline catalysts.

Introduction of the ester group $COOR_2$ for $R_1$ wherein $R_2$ is an alkyl group of 1-10 carbon atoms takes place by means of methods known to one skilled in the art. The carboxy compounds are reacted, for example, conventionally with diazohydrocarbons. Esterification with diazohydrocarbons is performed, for example, by mixing a solution of the diazohydrocarbon in an inert solvent, preferably in diethyl ether, with the carboxy compound in the same or in another inert solvent, e.g. methylene chloride. After the reaction is completed within 1-30 minutes, the solvent is removed and the ester purified as usual. Diazoalkanes are either known or can be prepared according to known methods [Org. Reactions 8:389-394 (1954)].

Introduction of the ester group $COOR_2$ for $R_1$ wherein $R_2$ represents a substituted or unsubstituted aryl group is performed according to the methods known to persons skilled in the art. For example, the carboxy compounds are reacted with the corresponding arylhydroxy compounds with dicyclohexylcarbodiimide in the presence of a suitable base, e.g. pyridine or triethylamine, in an inert solvent. Suitable solvents methylene chloride, ethylene chloride, chloroform, ethyl acetate, tetrahydrofuran, preferably chloroform. The reaction is conducted at temperatures of between $-30°$ C. and $+50°$ C., preferably at $+10°$ C.

The carbacyclin derivatives of general Formula I wherein $R_1$ means a carboxy group can be converted with suitable amounts of the corresponding inorganic bases into salts with neutralization taking place. For example, the solid inorganic salt is obtained when dissolving the corresponding PG acids in water containing the stoichiometric amount of the base, after evaporation of the water or after addition of a water-miscible solvent, e.g. alcohol or acetone.

The amine salts are prepared in the usual way. For this purpose, the PG acid is dissolved, for example, in a suitable solvent, such as ethanol, acetone, diethyl ether or benzene, and at least the stoichiometric quantity of the amine is added to this solution. During this step, the salt is ordinarily obtained in the solid form, or it is isolated in the usual manner after evaporation of the solvent.

The functional modification of the free OH-groups is performed according to methods known to one skilled in the art. For introduction of the ether blocking groups, for example, the reaction is carried out with dihydropyran in methylene chloride or chloroform with the use of an acidic condensation agent, such as, for example, p-toluenesulfonic acid. Dihydropyran is used in excess, preferably in 4 to 10 times the amount required theoretically. The reaction is normally finished at $0°$ C. to $30°$ C. after 15-30 minutes.

The acyl blocking groups are introduced by reacting a compound of general Formula I conventionally with a carboxylic acid derivative, e.g. an acid chloride, acid anhydride, and others.

Liberation of a functionally modified OH-group to obtain the compounds of general Formula I takes place according to known methods. For example, the cleavage of ether blocking groups is conducted in an aqueous solution of an organic acid, e.g. acetic acid, propionic acid, etc., or in an aqueous solution of an inorganic acid, e.g. hydrochloric acid. In order to improve solubility, a water-miscible inert organic solvent is suitably added. Organic solvents that can be used are, for example, alcohols, such as methanol and ethanol, and ethers, such as dimethoxyethane, dioxane and tetrahydrofuran. Tetrahydrofuranis employed with preference. The splitting off step is preferably performed at temperatures of between $20°$ C. and $80°$ C.

Cleavage of the silyl ether blocking groups is effected, for example, with tetrabutylammonium fluoride. Examples of suitable solvents are tetrahydrofuran, diethyl ether, dioxane, methylene chloride, etc. The splitting off step is preferably carried out at temperatures of between $0°$ C. and $80°$ C.

Saponification of the acyl groups takes place, for example, with alkali or alkaline earth carbonates or hydroxides in an alcohol or in the aqueous solution of an alcohol. Suitable alcohols are aliphatic alcohols, such as, for example, methanol, ethanol, butanol, etc., preferably methanol. Suitable alkali carbonates and hydroxides that can be cited are potassium and sodium salts, but the potassium salts are preferred. Examples of suitable alkaline earth carbonates and hydroxides are calcium carbonate, calcium hydroxide and barium carbonate. The reaction takes place at $-10°$ C. to $70°$ C., preferably at $25°$ C.

Introduction of the amide group $CONHR_3$ for $R_1$ takes place according to the methods with which a person skilled in the art is familiar. The carboxylic acids of general Formula I ($R_2$=H) are first converted in the presence of a tertiary amine, such as triethylamine, for example, with the isobutyl ester of chloroformic acid into the mixed anhydride. The reaction of the mixed anhydride with the alkali salt of the corresponding amide or with ammonia ($R_3$=H) takes place in an inert solvent or solvent mixture, e.g. tetrahydrofuran, dimethoxyethane, dimethylformamide, hexamethylphosphoric triamide, at temperatures of between $-30°$ C. and $+60°$ C., preferably at $0°$ C. to $30°$ C.

Another possibility of introducing the amide group $CONHR_3$ for $R_1$ resides in reacting a 1-carboxylic acid of general Formula I ($R_2$=H) wherein free hydroxy groups have been blocked intermediately with compounds of general Formula X

$$O=C=N-R_3 \qquad (X)$$

wherein $R_3$ has the meanings given above.

Reaction of the compound of general Formula I ($R_2$=COOH) with an isocyanate of general Formula VIII takes place optionally with the addition of a tertiary amine, such as, for example, triethylamine or pyridine. The reaction can be conducted without a solvent or in an inert solvent, preferably acetonitrile, tetrahydrofuran, acetone, dimethylacetamide, methylene chloride, diethyl ether, toluene, at temperatures of between $-80°$ C. to $100°$ C., preferably at $0°$ C. to $30°$ C.

In case the starting compound contains OH-groups in the prostane residue, these OH-groups are also made to react. If, in the final analysis, end products are desired which contain free hydroxy groups in the prostane residue, then starting compounds are suitably employed wherein these are intermediately blocked by preferably readily cleavable ether or acyl residues.

All other compounds of Formula I can be prepared according to methods disclosed in laid-open applications DOS 2,845,770, 3,237,200, 3,322,893, and 3,405,181.

The carbacyclins of Formula I wherein $R_9$ means the residue $R_6-(CH_2)_m-Z-$ with $R_6$ meaning $N_3$, Cl, Br, I, COOR$_2$-group, can be bound to polymeric carriers very readily without appreciable loss of biological activity. The novel carbacyclins prevent formation of thrombocyte aggregates on the surface of these polymeric carriers, such as, for example, vascular prostheses or artificial heart valves. After chemical linkage to proteins, the compounds of Formula I are suitable for the production of antibodies to prostacyclins of general Formula I.

The compounds of this invention are furthermore suitable for therapy of diseases of the cardiovascular system, of the stomach, the pancreas, the liver, and the kidneys. They have a hypotensive and bronchodilatory activity. They are furthermore suitable for inhibition of thrombocyte aggregation. Consequently, the novel carbacyclin derivatives of Formula I constitute valuable pharmaceutically active agents. Moreover, they show, as compared with corresponding prostaglandins and prostacyclins, with a similar spectrum of activity, a higher specificity and, above all, a substantially longer duration of effectiveness. They are distinguished by higher stability in comparison with PGI$_2$. The high tissue specificity of the novel carbacyclins is demonstrated in a study on smooth muscle organs, such as, for example, on the guinea pig ileum or on the isolated rabbit trachea where a substantially lower stimulation can be observed than in the administration of natural prostaglandins of the E-, A- or F-type.

The novel carbacyclin analogs exhibit the properties typical for prostacyclins, such as, for example, lowering of peripheral arterial and coronary vascular resistance, inhibition of thrombocyte aggregation and dissolution of platelet thrombi, myocardial cytoprotection, lowering of systemic blood pressure without simultaneously decreasing stroke volume and coronary blood flow; treatment for stroke, prophylaxis and therapy of coronary heart disease, coronary thrombosis, of therapy of coronary heart disease, coronary thrombosis, of cardiac infarction, peripheral arterial diseases, arteriosclerosis and thrombosis, prophylaxis and therapy of ischemic attacks on the CNS system, therapy for shock, inhibition of bronchoconstriction, inhibition of gastric acid secretion, and cytoprotection of the gastric and intestinal mucosa, cytoprotection in the liver, the pancreas and in the kidneys, antiallergic properties, lowering of pulmonary vascular resistance and of pulmonary blood pressure, promotion of renal blood flow, utilization in place of heparin or as adjuvant in dialysis or hemofiltration, preservation of stored blood plasma, especially stored blood platelets, inhibition of labor, treatment of gestational toxicosis, enhancement of cerebral blood circulation, treatment of asthma, etc. The novel carbacyclin analogs furthermore exhibit antiproliferative properties. The novel carbacyclins can also be used in combination, for example, with $\beta$-blockers or diuretics.

The novel carbacyclins are additionally distinguished by suppressing rejection reactions and by their antimetastatic activity. They keep Botallo's duct open (before surgery). They are furthermore suitable for treatment of diarrhea and for improving bowel movement.

The dosage of the compounds is 1–1,500 μg/kg/day if administered to human patients. The unit dosage for the pharmaceutic, acceptable carrier is 0.01–100 mg.

Upon intravenous injection into nonanesthetized, hypertonic rats in doses of 5, 20 and 100 μg/kg of body weight, the compounds according to the invention show a stronger blood-pressure-lowering and longer-lasting activity than PGE$_2$ and PGA$_2$ without triggering diarrhea, as does PGE$_2$, or cardiac arrhythmias, as does PGA$_2$.

Upon intravenous injection administered to anesthetized rabbits, the compounds of this invention exhibit, as compared with PGE$_2$ and PGA$_2$, a stronger and also considerably longer lasting lowering of the blood pressure without affecting other smooth-muscle organs or organ functions.

Sterile, injectable, aqueous or oily solutions are used for parenteral administration. Suitable for oral administration are, for example, tablets, dragees, or capsules.

The invention accordingly also concerns medicinal agents based on the compounds of general Formula I and conventional auxiliary agents and excipients.

The active compounds of this invention are to serve, in conjunction with the auxiliary agents known and customary in galenic pharmacy, for example, for the preparation of hypotensives.

The unit dosage range for an ampoule is 0.1–0.5 mg, for a tablet, 01,–1 mg.

The novel carbacyclins bind, with an only small loss of biological activity, to polymeric carriers. Thus, the compound set forth in Example 1 inhibits thrombocyte aggregation in a concentration of IC$_{50}$=1.7·16$^{-8}$M (0.14×iloprost). The compound of Formula I is furthermore suitable for determination of potential prosta- and carbacyclins on the prostacyclin receptor.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 37 25 031.0, are hereby incorporated by reference.

EXAMPLE 1

5(Z)-[1(S,$\beta$)-[5-Azido-1-pentynyl]-6$\beta$-[(E)-3$\alpha$-hydroxy-4-methyloct-6-yn-1-enyl]-7$\alpha$-hydroxy-bicyclo[3.3.0]octan-3-ylidene]pentanoic Acid 1a A solution cooled to −40° C. of 4.20 g (13.0 mmol) of 1-pentyn-5-yl-tert-butyldiphenylsilyl ether in 25 ml of anhydrous diethyl ether was combined with 8.4 ml of a 1.54-molar solution of n-butyllithium in hexane and, after stirring for 30 minutes, with 13 ml of a 1-molar solution of diethylaluminum chloride in toluene. After this addition, the mixture was allowed to warm up to 0°–3° C. and to react for another 45 minutes. The resultant emulsion was added to a mixture of 352 mg (1.37 mmol) of nickel acetylacetonate which had been made into a slurry in 25 ml of anhydrous diethyl ether and combined with 1.3 ml of a 1-molar solution of diisobutyl aluminum hydride in toluene; the mixture was cooled to −10° C. and a solution of 2.40 g (5.42 mmol) of 7-[(R,$\alpha$)-(tetrahydropyran-2-yloxy)-6$\beta$-[(E)-4-methyl-3$\alpha$-(tetrahydropyran-2-yloxy)oct-6-yn-1-enyl]bicyclo-[3.3.0]oct-1-en-3-one in 25 ml of anhydrous diethyl ether was added dropwise thereto without delay. The mixture was allowed to react for another 1.5 hours at −10° C. to −5° C., then quenched by pouring into a well-stirred mixture of about 300 ml of finely crushed ice and 100 ml of 0.5N HCl, repeatedly extracted with, in total, 400 ml of diethyl ether, the combined organic extracts were washed first with water, then with saturated NaCl solution to neutral reaction, dried over magnesium sulfate, and the solvent was removed by a water-jet aspirator.

The brown crude oil was chromatographed under pressure on a silica gel column with the use of an n-hexane/ethyl acetate gradient system.

In this way, 2.20 g (2.88 mmol, 53%) of still slightly contaminated 1(S,β)-[5-tert-butyldiphenylsilyl-oxy-1-pentynyl]-7α-tetrahydropyran-2-yloxy-6β-[(E)-3α-(tetrahydropyran-2-yloxy)-4-methyloct-6-yn-1-enyl]bicyclo[3.3.0]oct-1-en-3-one was isolated.

IR (film): 3065, 3040, 2820–2980, 1740, 1590, 1425, 1200, 1108, 1075, 1020, 970, 868, 820, 740 and 700 cm$^{-1}$.

1b

An emulsion of 2.46 g of 55% strength NaH dispersion in white oil was combined with 160 ml of anhydrous DMSO; the mixture was allowed to react for one hour at 23° C. and then combined in portions within 5 minutes with, in total, 13.1 g (29.6 mmol) of carboxybutyltriphenylphosphonium bromide. Subsequently a solution of the ketone prepared in 1a in 50 ml of DMSO was added dropwise thereto within 45 minutes, and the mixture was reacted for 28 hours at 50°–55° C. The reaction mixture was poured on a blend of about 200 ml of ice and 200 ml of water, set to pH 6 with saturated citric acid, and extracted repeatedly with, in total, 400 ml of diethyl ether. Further processing was performed as described in 1a. The resultant crude product was chromatographed under pressure on a silica gel column with the use of a dichloromethane/ethanol gradient system, thus isolating 1.64 g (1.93 mmol, 67%) of 5(E/Z)-[1(S,β)-[5-tert-butyldiphenylsilyloxy-1-pentynyl]-6β-[(E)-3β-(tetrahydropyran-2-yloxy)-4-methyloct-6-yn-1-enyl]-7α-(tetrahydropyran-2-yloxy)-bicyclo[3.3.0]octan-3-ylidene]pentanoic acid.

IR (film): 2600–3600, 3070, 3050, 2820–2980, 1710, 1590, 1428, 1260, 1200, 1110, 1020, 970, 870, 820, 738 and 704 cm$^{-1}$.

1c 780 mg (0.92 mmol) of the carboxylic acids isolated in 1b were esterified with an ether solution of diazomethane and, after chromatographic purification on a silica gel column with the use of a mobile phase mixture of n-hexane/ethyl acetate, 649 mg (0.75 mmol, 82%) of a clean 5(E/Z)-[1(S,β)-[5-tert-butyldiphenylsilyloxy-1-pentynyl]-6β-[(E)-3α-(tetrahydropyran-2-yloxy)-4-methyl-oct-6-yn-1-enyl]-7α-(tetrahydropyran-2-yloxy)-bicyclo-[3.3.0]octan-3-ylidene]pentanoic acid methyl ester was isolated.

IR (film): 3070, 3040, 2820–2980, 1738, 1590, 1428, 1200, 1110, 1075, 1020, 972, 870, 820, 740 and 703 cm$^{-1}$.

1d 146 mg (169 μmol) of the methyl ester described in 1c was dissolved in 30 ml of anhydrous tetrahydrofuran, combined with 0.3 ml of a 1-molar tetrabutylammonium fluoride solution in tetrahydrofuran, and stirred at 23° C. for 18 hours. The mixture was quenched by adding 30 ml of a 10% strength aqueous ammonium chloride solution and repeatedly extracted with, in total, 80 ml of diethyl ether. The organic extracts were washed with saturated NaCl solution, dried over magnesium sulfate, and the crude product, obtained by evaporation of the solvent under a water jet vacuum, was purified by chromatography on 6 TLC plates with a 1:1 mixture of n-hexane/ethyl acetate. After elution with diethyl ether, 91 mg (146 μmol, 86%) of 5(E/Z)-[1(S,β)-[5-hydroxy-1-pentynyl]-6β-[(E)-3α-(tetrahydropyran-2-yloxy)-4-methyloct-6-yn-1-enyl]-7α-(tetrahydropyran-2-yloxy)bicyclo[3.3.0]octan-3-ylidene]pentanoic acid methyl ester was isolated.

IR (film): 3200–3650, 2820–2980, 1740, 1430, 1200, 1075, 1020, 970, 902, 867 and 815 cm$^{-1}$.

1e

The alcohol obtained in 1d was dissolved in 11 ml of anhydrous acetonitrile and combined in succession with 484 mg (1.46 mmol) of tetrabromomethane, 117 μl (1.45 mmol) of pyridine, 382 mg (1.46 mmol) of triphenylphosphine, 335 μl (1.45 mmol) of collidine, and allowed to react for one hour at 23° C. The mixture was combined with 2 ml of water, 1 ml of 0.5N hydrochloric acid, 2 drops of an aqueous 10% Na$_2$S$_2$O$_3$ solution, and the mixture was repeatedly extracted with 100 ml of diethyl ether. After the usual working up procedure, the crude product was purified by chromatography on 9 TLC plates with the use of a 4:1 mixture of n-hexane/ethyl acetate. After elution with diethyl ether, 93 mg (136 μmol, 93%) of 5(E/Z)-[1(S,β)-[5-bromo-1-pentynyl]-6β-[(E)-3α-(tetrahydropyran-2-yloxy)-4-methyloct-6-yn-1-enyl]-7α-(tetrahydropyran-2-yloxy)-bicyclo[3.3.0]octan-3-ylidene]pentanoic acid methyl ester was isolated.

IR (film): 2820–2980, 1740, 1452, 1375, 1200, 1160, 1125, 1075, 1020, 975, 906, 870 and 815 cm$^{-1}$.

1f

The bromides obtained in 1e were dissolved in 9 ml of anhydrous dimethylformamide, combined with 38 mg (585 μmol) of sodium azide, and the mixture was allowed to react for 3.5 hours at 60° C. The mixture was combined with 60 ml of water, repeatedly extracted with, in total, 100 ml of diethyl ether, washed with saturated NaCl, dried over magnesium sulfate, and the solvent was removed by a water jet aspirator, thus isolating 141 mg of crude 5(E/Z)-[1(S,β)-[5-azido-1-pentynyl]-6β-[(E)-3α-(tetrahydropyran-2-yloxy)-4-methyloct-6-yn-1-enyl]-7α-(tetrahydropyran-2-yloxy)-bicyclo[3.3.0]octan-3-ylidene]pentanoic acid methyl ester which was reacted further without purification.

1g

The azides obtained in 1f were combined with 18 ml of a 65:35:10 mixture of glacial acetic acid/water/tetrahydrofuran and agitated at 23° C. for 23 hours. The mixture was concentrated under a water jet vacuum at 40° C. and any still contained acetic acid was removed by means of azeotropic distillation by repeated addition of toluene. The thus-obtained crude product was purified by chromatography on 9 TLC plates with the use of a 95:5 mixture of dichloromethane/ethanol as the mobile phase, and diethyl ether as the eluent. In this way, 51 mg (106 μmol, 78% based on the educt from 1f) of 5(E/Z)-[1(S,β)-[5-azido-1-pentynyl]-6β-[(E)-3α-hydroxy-4-methyloct-6-yn-1-enyl]-7α-hydroxybicyclo[3.3.0]octan-3-ylidene]pentanoic acid methyl ester was isolated.

IR (film): 3200–3600, 2820–2980, 2100, 1734, 1200, 1085, 1030, 1020 and 970 cm$^{-1}$.

1h 50 mg of the methyl esters isolated in 1g was dissolved in 6 ml of methanol, combined with 4 ml of a 5% aqueous lithium hydroxide solution, adjusted to pH 3–4 after 4 hours of stirring at 23° C. by a saturated citric acid, extracted repeatedly with trichloromethane, and the combined organic extracts were dried over magnesium sulfate. The crude product obtained after withdrawing the solvent under a water jet vacuum was separated by chromatography on 4 silica gel plates with the use of a 9:1 mixture of dichloromethane/ethanol, developing twice, and elution with trichloromethane/isopropanol. After evaporation of the solvent, 17 mg (36 μmol, 35%) of 5(E)-[1(S,β)-[5-azido-1-pentynyl]-6β-[(E)-3α-hydroxy-4-methyl-oct-6-yn-1-enyl]-7α-hydroxybicyclo[3.3.0]octan-3-ylidene]pentanoic acid, as well as 19 mg (41 μmol, 39%) of the title compound were isolated.

IR (film): 2450–3700, 2820–2980, 2100, 1710, 1570, 1430, 1410, 1295, 1280, 1095, 1075, 1018 and 970 cm$^{-1}$.

EXAMPLE 2

5(E/Z)-[1(S,β)-[4-Carboxy-1-butynyl]-6β-[(E)-3α-hydroxy-4-methyloct-6-yn-1-enyl]-7α-hydroxy-bicyclo[3.3.0]octan-3-ylidene]pentanoic Acid Methyl Ester 2a 193 mg (309 μmol) of 5(E/Z)-[1(S,β)-[5-hydroxy-1-pentynyl]-6β-[(E)-3α-(tetrahydropyran-2-yloxy)-4-methyloct-6-yn-1-enyl]-7α-(tetrahydropyran-2-yloxy)bicyclo[3.3.0]octan-3-ylidene]pentanoic acid methyl ester was dissolved in 25 ml of acetone, cooled to −30° C., combined with 600 μl of Jones reagent, and allowed to react for 3 hours at −30° C. to −20° C. Excess oxidizing agent was removed by adding 2 ml of isopropanol, the mixture was allowed to heat up to 20° C., diluted with water, and extracted with dichloromethane. The combined organic extracts were first washed with water, then with saturated NaCl solution until a neutral reaction was obtained, dried over magnesium sulfate, and the crude oil obtained after evaporation of the solvent was purified by chromatography on 10 silica gel plates. The mobile phase was a 2:8 mixture of n-hexane/ethyl acetate; the eluent was a mixture of trichloromethane/isopropanol. Besides 30 mg of starting material, 157 ml (246 μmol, 80%) of 5(E/Z)-[1(S,β)-[4-carboxy-1-butynyl]-6β-[(E)-3α-(tetrahydropyran-2-yloxy)-4-methyloct-6-yn-1-enyl]-7α-(tetrahydropyran-2-yloxy)bicyclo[3.3.0]octan-3-ylidene]pentanoic acid methyl ester was isolated.

IR (film): 2500–3600, 2820–2980, 1732, 1710, 1435, 1265, 1200, 1130, 1020, 974, 904, 867 and 812 cm$^{-1}$.

2b

In analogy to Example 1g, the tetrahydropyranyl ethers were split off the product obtained in 2a. After chromatographic purification on 7 silica gel plates with a 95:5 mixture of dichloromethane/methanol, developing twice, and elution with an 8:2 mixture of dichloromethane/isopropanol, 69 mg (146 μmol, 60%) of the title compound was isolated besides 47 mg of starting material.

IR (film): 3100–3500, 2500–3650, 2820–2980, 1735, 1710, 1435, 1260, 1200, 1074, 1020, 970 and 902 cm$^{-1}$.

EXAMPLE 3

5(E/Z)-[(1S,β)-[4-Carboxy-1-butynyl]-6β-[(E)-3α-hydroxy-4-methyloct-6-yn-1-enyl]-7α-hydroxybicyclo[3.3.0]octan-3-ylidene]pentanoic Acid In analogy to Example 1h, 14 mg (30 μmol) of the title compound obtained according to Example 2 was reacted, thus isolating after an analogous working up process 13 mg (29 μmol, 95%) of the title compound.

IR (film): 2500–3650, 2820–2980, 1712, 1570, 1435, 1075, 1020, 970 cm$^{-1}$.

EXAMPLE 4

5(Z)-{1(S,beta)-[5-Bromo-1-pentinyl]-6beta-[(E)]-3alpha-hydroxy-4-methyl-oct-6-in-1-enyl]-7alpha-hydroxy-bicyclo[3.3.0]octan-3-ylidene}-pentanoic acid (A) and 5(E)-{1(S,beta)-[5-bromo-1-pentinyl]-6beta-[(E)-3alpha-hydroxy-4-methyl-oct-6-in-1-enyl]-7alpha-hydroxy-bicyclo[3.3.0]octan-3-ylidene}-pentanoic acid (B)

4a) 86 mg (125 micromol) of the bromide prepared according to Example 1e is reacted analogously to Example 1g and, after working up and purification, 62 mg (119 micromol, 96%) of 5(E/Z)-{(1(S,beta)-[5-bromo-1-pentinyl]-6beta-[(E)-3alpha-hydroxy-4-methyl-oct-6-in-1-enyl]-7alpha-hydroxy-bicyclo[3.3.0]octan-3-ylidene)-pentanoic acid methyl ester is isolated.

IR (film): 3600–3200, 2940, 2850, 1735, 1430, 1245, 1170, 1075, 1010, 970 and 730 cm$^{-1}$.

4b) 62 mg (119 micromol) of the compound prepared under Example 4a is saponified analogously to Example 1h. After working up and chromatographic isomeric separation on 2 analytical thin-layer plates with a mixture of dichloromethane and ethanol, 14 mg (28 micromol, 23%) of title compound B is isolated as nonpolar component as well as 24 mg (47 micromol, 39%) of title compound A as polar component besides 18 mg of a mixed fraction of A and B.

IR (film) of A: 3600–2400, 2960, 2930, 2240, 1710, 1430, 1250, 1090, 1075, 1010, 970 and 805 cm$^{-1}$.

IR (film) of B: 3600–2400, 2960, 2920, 2230, 1710, 1430, 1250, 1090, 1080, 1010, 970 and 805 cm$^{-1}$.

EXAMPLE 5

5(Z)-{1(S,beta)-[5-Iodo-1-pentinyl]-6beta-[(E)-3alpha-hydroxy-4-methyl-oct-6-in-1-enyl]-7alpha-hydroxy-bicyclo[3.3.0]octan-3-ylidene} pentanoic acid 7.1 mg (14 micromol) of 5(Z)-{(1(S,beta)-[5-bromo-1-pentinyl]-6beta-[(E)-3alpha-hydroxy-4-methyl-oct-6-in-1-enyl]-7alpha-hydroxy-bicyclo[3.3.0]octan-3-ylidene} pentanoic acid is dissolved in 100 micromol of acetone, mixed with 150 micromol of 50% solution of sodium iodide in acetone and stirred at 23° C. 3 to 4 hours under an atmosphere of dry argon. It is purified by chromatography on an analytical thin-layer plate with a mixture of dichloromethane and ethanol and 6.2 mg (11 micromol, 80%) of the title compound is isolated.

IR (CHCl$_3$): 3600–2400, 2960, 2930, 2240, 1710, 1450, 1430, 1345, 1330, 1250, 1220, 1170, 1095, 1075, 1010 and 970 cm$^{-1}$.

EXAMPLE 6

5(E)-{1(S,beta)-[5-Iodo-1-pentinyl]-6beta-[(E)-3alpha-hydroxy-4-methyl-oct-6-in-1-enyl]-7alpha-hydroxy-bicyclo[3.3.0]octan-3-ylidene) pentanoic acid 8 mg (16 micromol) of 5(E)-{1(S,beta)-[5-bromo-1-pentinyl]-6beta-[(E)-3alpha-hydroxy-4-methyl-oct-6-in-1-enyl]-7alpha-hydroxy-bicyclo[3.3.0]octan-3-ylidene} pentanoic acid is reacted analogously to Example 5 and 5.1 mg (9 micromol, 58%) of the title compound is isolated after chromatographic purification.

IR (film): 3600–2400, 2960, 2920, 2230, 1710, 1450, 1430, 1345, 1330, 1250, 1220, 1170, 1090, 1070, 1005 and 970 cm$^{-1}$.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A carbacyclin derivative of Formula I

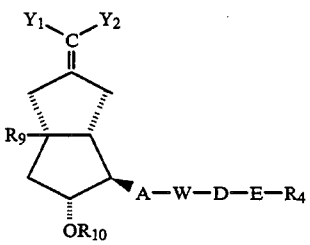

wherein $Y_1$ is the residue —$CH_2$—X—$(CH_2)_n$—$R_1$ or the residue

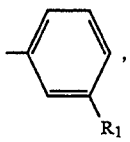

n is 1 or 3, $R_1$ is —$COCH_3$; —$COOR_2$ wherein $R_2$ is hydrogen; $C_{4-10}$-cycloalkyl; $C_6$-$C_{10}$-aryl optionally substituted by 1-3 halogen atoms, a phenyl group, 1-3 $C_1$-$C_4$-alkyl groups, a chloromethyl, a monofluoromethyl, a trifluoromethyl, a carboxy, a hydroxy or a $C_1$-$C_4$-alkoxy group; or alkyl of 1-10 carbon atoms optionally substituted by halogen, phenyl, $C_1$-$C_4$-alkoxy or $C_1$-$C_4$-dialkylamino; or the residue —$CONHR_3$ wherein $R_3$ is hydrogen or an alkanoyl or alkanesulfonyl residue of respectively 1-10 carbon atoms, $R_9$ is the residue —Z—$(CH_2)_m$—$R_6$, m is 2-10, Z is a —C≡C—, a cis-CH=CH— or a trans-CH=CH— group, $R_6$ is Cl, Br, I or $COOR_{2a}$, $R_{2a}$ is hydrogen or a methyl or ethyl group, X is an oxygen atom or a methylene group, $Y_2$ is hydrogen or fluorine, A is a —$CH_2$—$CH_2$—, trans-CH=CH— or —C≡C— group, W is a —CH($OR_{10}$)-group or a

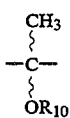

group wherein the $OR_{10}$ group can be in the α- or β-position,

D is the group

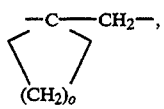

a straight-chain, saturated alkylene group of 1-5 carbon atoms, a branched, saturated or a straight-chain or branched, unsaturated alkylene group of 2-5 carbon atoms which can optionally be substituted by fluorine atoms, o is 1, 2 or 3, E is a direct bond, a —C≡C-group or a —CH=$CR_7$-group wherein $R_7$ is a hydrogen atom, an alkyl group of 1-5 carbon atoms or halogen, $R_4$ is an alkyl group of 1-10 carbon atoms; a cycloalkyl group of 3-10 carbon atoms; or a $C_6$-$C_{10}$-aryl group optionally substituted by 1-3 halogen atoms, a phenyl group, 1-3 $C_1$-$C_4$-alkyl groups, a chloromethyl, a monofluoromethyl, a trifluoromethyl, a carboxy, a hydroxy or a $C_1$-$C_4$-alkoxy group, $R_{10}$ is H or tetrahydropyranyl, tetrahydrofuranyl, α-ethoxyethyl, trimethylsilyl, dimethyl-tert-butylsilyl, tri-p-benzylsilyl, acetyl, propionyl, butyryl or benzoyl residues, and, if $R_2$ is a hydrogen atom, a salt thereof with a physiologically compatible base, or a cyclodextrin clathrate thereof.

2. 5(E/Z)-[1(S,β)-[4-Carboxy-1-butynyl]-6β-[(E)-3α-hydroxy-4-methyloct-6-yn-1-enyl]-7α-hydroxybicyclo[3.3.0]octan-3-ylidene]pentanoic acid methyl ester, a compound of claim 1.

3. 5(E/Z)-[1(S,β)-[4-Carboxy-1-butynyl]6β-[(E)-3α-hydroxy-4-methyloct-6-yn-1-enyl]-7α-hydroxybicyclo[3.3.0]octan-3-ylidene]pentanoic acid, a compound of claim 1.

4. 5(E)-[1(S,β)-[5-Hydroxy-1-pentynyl]-6β-[(E)-3α-hydroxy-4-methyloct-6-yn-1-enyl]-7α-hydroxybicyclo[3.3.0]octan-3-ylidene]pentanoic acid.

5. A carbacyclin derivative of Formula I

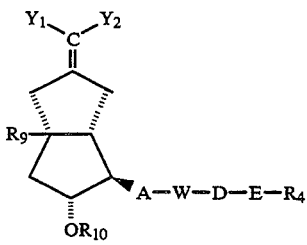

wherein $Y_1$ is the residue —$CH_2$—X—$(CH_2)_n$—$R_1$ or the residue

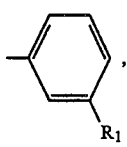

n is 1 or 3, $R_1$ is the residue the residue

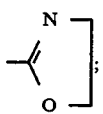

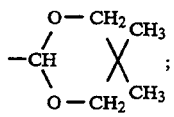

—COCH$_3$; —COOR$_2$ wherein —COCH$_3$; —COOR$_2$ wherein

R$_2$ is hydrogen; C$_{4-10}$-cycloalkyl; C$_6$–C$_{10}$-aryl optionally substituted by 1–3 halogen atoms, a phenyl group, 1–3 C$_1$–C$_4$-alkyl groups, a chloromethyl, a monofluoromethyl, a trifluoromethyl, a carboxy, a hydroxy or a C$_1$–C$_4$-alkoxy group; a heterocyclic residue selected from 2-furyl, 3-furyl, 2-thienyl, 3-thienyl, 2-pyridyl, 3-pyridyl, or 4-pyridyl; or alkyl of 1–10 carbon atoms optionally substituted by halogen, phenyl, C$_1$–C$_4$-alkoxy or C$_1$–C$_4$-dialkylamino; or the residue —CONHR$_3$ wherein R$_3$ is hydrogen or an alkanoyl or alkanesulfonyl residue of respectively 1–10 carbon atoms, R$_9$ is the residue —Z—(CH$_2$)$_m$—R$_6$, m is 2–10, Z is a —C≡C—, a cis-CH=CH— or a trans-CH=CH— group, R$_6$ is Cl, Br, I or COOR$_{2a}$, R$_{2a}$ is hydrogen or a methyl or ethyl group, X is an oxygen atom or a methylene group, Y$_2$ is hydrogen or fluorine, A is a —CH$_2$—CH$_2$—, trans-CH=CH— or —C≡C- group, W is a —CH(OR$_{10}$)-group or a

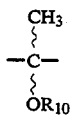

group wherein the OR$_{10}$ group can be in the α- or β-position,

D is the group

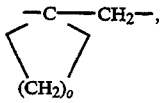

a straight-chain, saturated alkylene group of 1–5 carbon atoms, a branched, saturated or a straight-chain or branched, unsaturated alkylene group of 2–5 carbon atoms which can optionally be substituted by fluorine atoms, o is 1, 2 or 3, E is a direct bond, a —C≡C-group or a —CH=CR$_7$-group wherein R$_7$ is a hydrogen atom, an alkyl group of 1–5 carbon atoms or halogen, R$_4$ is an alkyl group of 1–10 carbon atoms; a cycloalkyl group of 3–10 carbon atoms; or a C$_6$–C$_{10}$-aryl group optionally substituted by 1–3 halogen atoms, a phenyl group, 1–3 C$_1$–C$_4$-alkyl groups, a chloromethyl, a monofluoromethyl, a trifluoromethyl, a carboxy, a hydroxy or a C$_1$–C$_4$-alkoxy group; or a 2-furyl, 2-thienyl, 2-pyridyl, 3-pyridyl, 4-pyridyl, 3-furyl or 3-thienyl group, R$_{10}$ is H or tetrahydropyranyl, tetrahydrofuranyl, α-ethoxyethyl, trimethylsilyl, dimethyl-tert-butylsilyl, tri-p-benzylsilyl, acetyl, propionyl, butyryl or benzoyl residues, and, if R$_2$ is a hydrogen atom, a salt thereof with a physiologically compatible base, or a cyclodextrin clathrate thereof.

6. A compound of claim 5, wherein R$_2$ is —COCH$_3$, —COOR$_2$ or the residue —CONHR$_3$.

7. A compound of claim 1 having at least one acid and/or ester group.

8. A compound of claim 5 having at least one acid and/or ester group.

9. A pharmaceutical agent comprising a compound of claim 1 and a pharmaceutically acceptable or excipient.

10. A pharmaceutical agent comprising a compound of claim 5 and a pharmaceutically acceptable or excipient.

* * * * *